Figure 1:
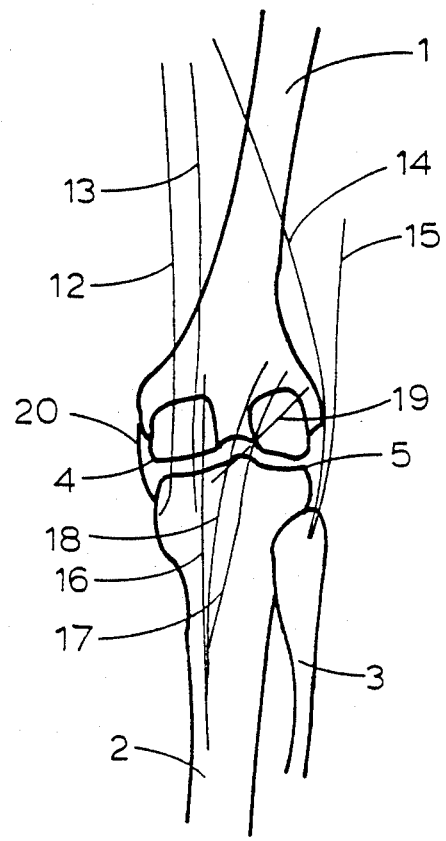

United States Patent [19]

Huntjens

[11] Patent Number: 4,724,831
[45] Date of Patent: Feb. 16, 1988

[54] KNEE SUPPORT FOR AIDING PROPRIOCEPTIVE INNERVATION

[75] Inventor: Jozef H. G. Huntjens, Schinnen, Netherlands

[73] Assignee: MacIntosh N.V., Stein, Netherlands

[21] Appl. No.: 903,492

[22] Filed: Sep. 4, 1986

[30] Foreign Application Priority Data

Sep. 17, 1985 [NL] Netherlands ............ 8502535

[51] Int. Cl.⁴ ............ A61F 3/00; A61F 13/06
[52] U.S. Cl. .................... 128/80 C; 128/165
[58] Field of Search .......... 128/80 R, 80 C, 80 F, 128/156, 165, 166, 166.5

[56] References Cited

U.S. PATENT DOCUMENTS

| | | | |
|---|---|---|---|
| 3,046,981 | 7/1962 | Biggs, Jr. et al. | 128/80 C |
| 3,934,583 | 1/1976 | Hollingshead et al. | 128/80 C X |
| 4,323,058 | 4/1982 | Detty | 128/80 H |
| 4,370,978 | 2/1983 | Palumbo | 128/80 C |
| 4,425,912 | 1/1984 | Harper | 128/80 C |
| 4,492,227 | 1/1985 | Senn et al. | 128/80 C X |
| 4,550,721 | 11/1985 | Michel | 128/80 E |

FOREIGN PATENT DOCUMENTS 0027172 4/1981 European Pat. Off. .
2553996 5/1985 France .................... 128/80 C Primary Examiner—Clifford D. Crowder
Attorney, Agent, or Firm—Cushman, Darby & Cushman

[57] ABSTRACT

Support for a knee joint comprising a wrapper or sleeve substantially made from elastic material, extending after its application between a limit proximal and a limit distal in respect of the knee joint, which support has an opening to leave the knee cap free and which support may be provided with one or more bandages to apply pressure to parts of the area of the knee joint. The inner surface of the support is provided with surface parts having an increased coefficient of friction in respect of the skin when compared with the rest of the inner surface. These parts of the surface occur in those places that are in contact, after the application of the support, with parts of the skin surface in the area round the joint under which tissue occurs of muscles and tendons that is to be subjected to proprioceptice innervation, which muscles and tendons extend from the leg below and the leg above the knee beyond the articular surfaces of the knee between the femur and the tibia. The parts of the surface having an increased coefficient of friction in respect of the skin, consist of chamois leather.

9 Claims, 8 Drawing Figures

KNEE SUPPORT FOR AIDING PROPRIOCEPTIVE INNERVATION

The invention relates to a support for a knee joint comprising a wrapper or sleeve made substantially from elastic material, extending after its application between a limit proximal and a limit distal in respect of the knee joint, which support has an opening to leave the knee cap free and which support may be provided with bandages to apply pressure to parts of the area of the knee joint.

Such a support is known from U.S. Pat. No. A-3,046,981. These braces have the property of exclusively mechanically providing, after their application round the weak or damaged knee, an increased stability to the knee joint through the sleeve or wrapper, optionally in addition using one or more bandages.

The invention provides a support for a knee with the body itself being stimulated to contribute to the increased stability.

This is achieved in that the inner surface of the support is provided with surface parts having an increased coefficient of friction in respect of the skin when compared with the rest of the inner surface and in that these parts of the surface occur in those places that are in contact, after the application of the support, with parts of the skin surface in the area round the joint under which tissue occurs of muscles and tendons that is to be subjected to proprioceptive innervation, which muscles and tendons extend from the leg below and the leg above the knee beyond the articular surfaces of the knee between the femur and the tibia.

Proprioceptive innervation of the musculature is understood to means in this connection the increase in the tonus or muscular tension by proprioceptively sensible receptors present in the muscular or tendinous tissue passing stimuli on to the central nervous system, which in its turn influences the muscular action. The proprioceptive sensibility must be distinguished from the exteroceptive sensibility with the stimuli from the body itself are further conveyed to the central nervous system.

The invention utilized the presence of proprioceptive sensibility. Care is taken that particular parts of the skin having, underneath, receptors to be stimulated should be covered with material having a very low slipping effect on the skin, sticking to the skin as it were. When the area round the joint is moved, the skin is shifted to and fro and presses and massages the deeper tissue in which the receptors are contained. As a result, the muscle in which the receptors are contained is contracted and a higher tonus is brought about in the muscle and tendon. Now, by the continued simultaneous proprioceptive innervation of all tendons of the muscles acting on the knee joint, the tonus in the muscles and the tendons is increased so that a better natural bond is maintained between the parts forming the knee joint. The stability in standing and walking is thus improved so that the load on the ligaments is reduced.

In the specification following hereinafter the Latin nomenclature will be used to indicate the parts of the body if such is necessary for reasons of clarity, with the English names in brackets behind, if possible. Moreover, in the specification below the following is understood by distal: away from the trunk;
proximal: towards the trunk;
medial: on the inside of the part of the body (knee);
lateral: on the outside of the part of the body (knee);
dorsal: on the back of the part of the body (knee); and
ventral: on the front of the part of the body (knee).

These designations are used also in describing the support while it is considered as having been applied round the knee.

The parts of the surface having an increased coefficient of friction in respect of the skin are preferably formed pieces of chamois leather stuck or sown to the inside of the sleeve or wrapper. The fact is that the property of natural chamois leather is that already in dry condition it has a coefficient of friction in respect of the skin which is higher than that of the customary textile materials used for supports. When it becomes damp and wet, chamois leather shows an even much higher coefficient of friction, which is an advantage for the object of the invention, because the moisture content of the inside of a support applied to the skin will increase rapidly as a result of perspiration.

The part of the surface having an increased coefficient of friction may be discontinuous. This is an advantage when the part of the surface having an increased coefficient of friction consists of material less elastic than the material of the rest of the support.

The parts of the surface with an increased coefficient of friction preferably occur along the proximal and distal sides of the support coinciding with the proximal and distal limits of the support, round the opening for the knee cap and on strips extending between the proximal and distal limits of the support and situated medially and laterally in respect of the opening and near the opening.

The advantage of such a support is that it is suited for the vast majority of knee injuries. The fact is that the most frequent knee injury is the spraining or rupture of the ligamentum collaterale tibiale (inner collateral ligament) between the femur (thigh bone) and the tibia (shin bone). This injury is very often caused by an excessive inward rotation of the leg above the knee in respect of the leg below the knee with a fully stretched or slightly bent knee joint, or by a blow or impact from a lateral direction on the knee. Owing to this injury, the guiding of the knee joint in bending and stretching will be less good and check against rotation will be less good, which again may involve a risk of damage to the ligamentum collaterale fibulare (outer collateral ligament) between the femur and the fibula (calf bone). Damage to a cruciate ligament may be caused also.

In respect of the knee joint four principal movements may be distinguished, viz.

I stretching or extension;
II bending or flexion;
III with a bent knee, endorotation, i.e. an inward rotation of the leg below the knee, and
IV exorotation, i.e. an outward rotation of the leg below the knee.

In all knee positions the muscles acting on the knee joint provide an equilibrium. These muscles are mainly: (m. stands for musculum):

a. the m. quadriceps femoris consisting, among other parts, of:
  a.1. the m. rectus femoris;
  a.2. the m. vastus medialis;
  a.3. the m. vastus lateralis;
b. the m. sartorius (tailor's muscle)
c. the m. biceps femoris
d. the m. semitendinosus (semitendinous muscle)
e. the m. semimembranosus (semimembranous muscle)

f. the m. triceps surae comprising, among other parts:
   f.1. the m. gastrocnemius
   f.2. the m. plantaris
g. the m. gracilis, and
h. the m. popliteus.

In the said movement I, the extension, it is particularly muscles a.1. up to and including a.3. that are involved. In the said movement II, the flexion, muscles b., c., d., e., f.1., g. and h. are active. Movement III, the endorotation, is made possible by muscles b., d., e., g. and h. Muscle c., finally is active mainly in movement IV, the exorotation.

With their usually tendinous ends the said muscles reach into the area of the knee joint and extend beyond the articular surfaces between the tibia (shin bone) and the femur (thigh bone). In some cases these ends form part of the capsula articularis (joint capsule). These ends partly occur at the front of the knee, these are muscles a.1. up to and including a.3., another part is situated at the back of the knee, these are muscles c., d., e., f.1., f.2. ad h. The ends of muscles b. and g. mainly extend medially along the knee joint. It is noted also that the tendons of muscles a.3., respectively a.3., have a more medial, respectively more lateral, position, and that a few tendinous ends of the muscles occur partly at the back of the knee joint and partly in a lateral or medial position such as, for instance, those of muscle e. From the above it will be clear that round the area of the knee joint, in positions both proximal and distal in respect of the knee joint, as well as between these limits, there are tendinous ends of muscles acting on the knee joint, the tonus of which can be increased by proprioceptive innervation. Also the passive tonus, i.e. the tonus of an idle muscle.

A support for a knee joint particularly suited for applying the invention comprises a wrapper in the shape of a trapezium of which the slant sides are provided with semi-elliptic recesses, which wrapper, using fasteners along the slant sides, can be shaped to form a sleeve with an opening to leave the knee cap free, the proximal side of the support, i.e. the long side of the trapezium, and the distal side of the support, i.e. the short side of the trapezium, having a concave inward bent shape, at least in their central parts, and which support is provided with a medial pair of bandages fastened medially near the opening and consisting of a proximal and a distal bandage and with a lateral pair of bandages fastened laterally near the opening and consisting of a proximal and a distal bandage, the proximal and distal bandages being provided with fasteners by which they can be fastened in respectively proximal and distal positions in respect of the opening. The advantage of this support for a knee joint over existing supports is that by pulling and fastening the bandages from medial and lateral directions the knee cap is slightly raised from the articular surfaces of the femur cooperating with the knee cap. This raising is achieved because the medial and lateral sides of the opening for the knee are pulled towards each other and consequently pressed against the knee cap.

Owing to the presence of the concave parts of the proximal and distal sides of the support, resulting in a substantial narrowing of the dorsal side, an advantageous great pressure is exercised on the dorsal side of the knee when pulling the bandages secured on the medial and lateral sides. Yet another advantage of the concave parts of the proximal and distal sides of the support is that, during the bending of the knee, they enable these sides of the support to partly folow the simultaneous increase in the distance between the dorsal tendons of the m. biceps femoris and the m. semitendinosus. The fact is that the concave parts will then adapt a more shallow shape resulting, moreover, in a transversal elongation. Special measures in respect of the local elasticity need not be taken. All this is of particular importance if, according to the invention, at those places where this support is applied against the said muscles parts of the surface have an increased coefficient of friction to retain the skin. Without the said concave shape, when bending or stretching the knee, and excessive and consequently painful shifting would occur between the skin and the tendons.

This knee support already provides relief even without utilizing the proprioceptive action of the muscles in case of an inflammation of the articular cartilage beween the knee cap and the femur. To provide the inner surface of this support with parts having an increased coefficient of friction is an advantage, because in connection with its non-slip nature it is easier for the support to be aplied round the knee in the form of a wrapper than of a sleeve. Owing to the presence, round the opening, of a surface having an increased coefficient of friction, the grip on the skin will improve when pulling the bandages, so that the knee cap, too, is raised better. This is of particular importance, because as a result of the proprioceptive action of this support whose surface is provided also with additional parts having an increased coefficient of friction, an increased tonus is brought about in the muscles. This increased tonus, of course, also occurs in the tendon of the m. quadriceps incorporating the knee cap as a sesamoid bone. The more tension is exercised on the m. quadriceps the firmer the articular surfaces of the knee cap are pressed onto those of the femur. By raising the knee cap using the bandages of the proposed support this action is compensated to some degree, which is more comfortable for the user of the support.

The support can yet be improved upon by applying on the inner surface of the support, round the semi-elliptic recesses, pad-like elevations providing an even better grip on the skin round the knee cap. This effect can be enhanced by allowing the place where the inner surface round the semi-elliptic recesses is provided with parts having an increased coefficient of friction to coincide with the place where, round the semi-elliptic recesses, the pad-like elevations occur.

A central strip on the dorsal side of the support extending between the proximal and distal sides of the support is preferably in the form of a pad. The advantage is that after the application of the support greater pressure can be applied to the articular cavity in the poples. Moreover, the attainability of the tissue to be subjected to proprioceptive innervation at that place is improved.

As stated earlier, the support substantially consists of an elastic material. This may be a woven textile material based on cotton, wool or synthetic filaments, which is elastic in all directions. The material having an increased coefficient of friction in respect of the skin is, as stated, preferably natural chamois leather. Other materials also showing an increased coefficient of friction in respect of the skin in dry condition and in moist condition compared with the elastic material are suitable also. However, those materials that will have a lower coefficient of friction when they become moist are to be advised against, because that will make the intended effect uncertain. For instance, some artificial rubbers show this last-mentioned characteristic.

The invention will now be further elucidated with reference to a typical embodiment shown in the drawing.

In the drawing

Figure 2:
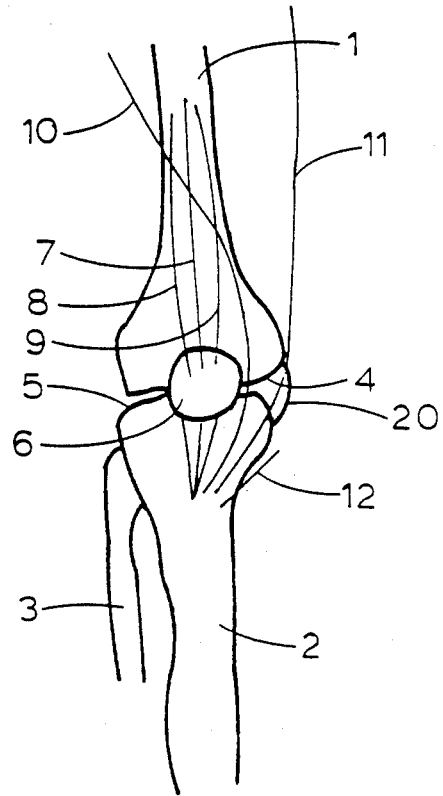
Figure 3:
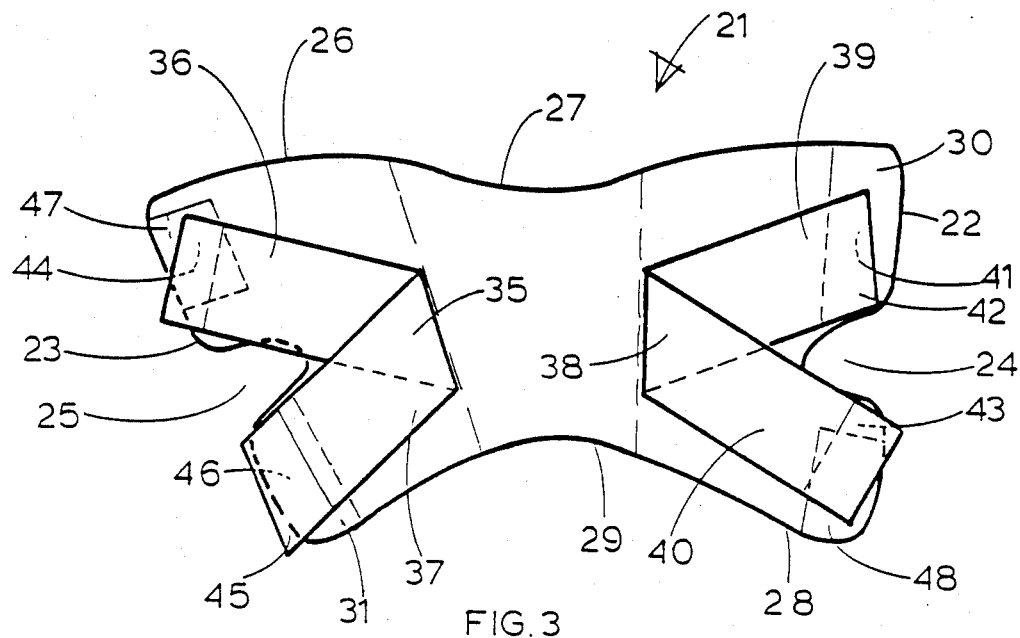
Figure 4:
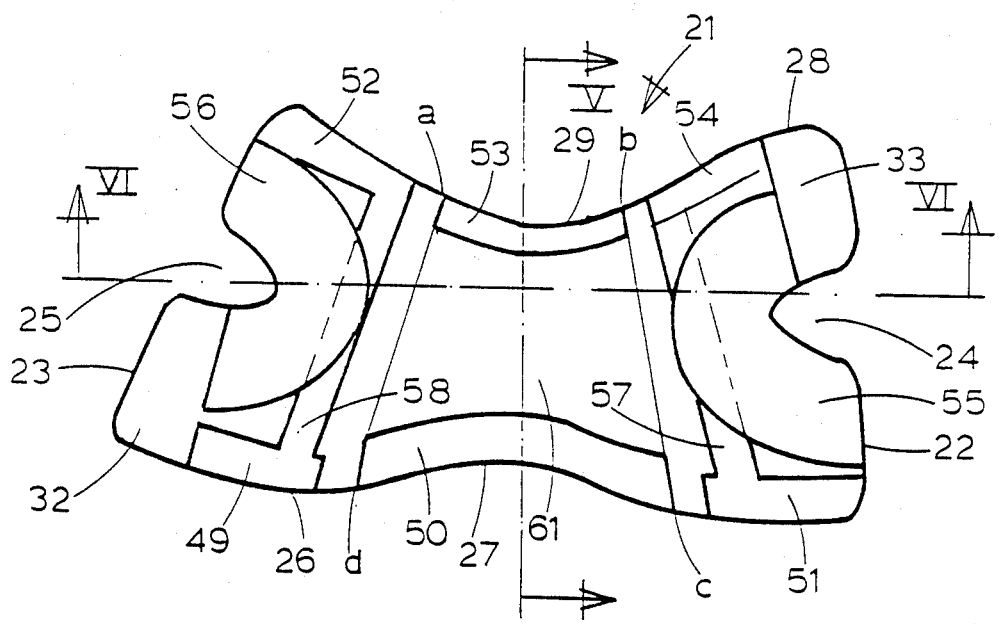
Figure 5:
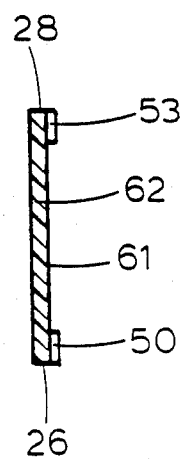
Figure 6:
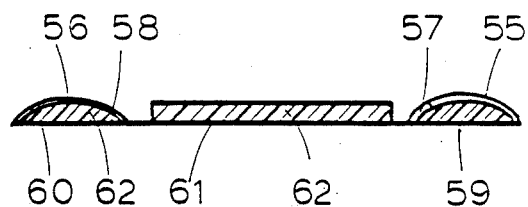
Figure 7:
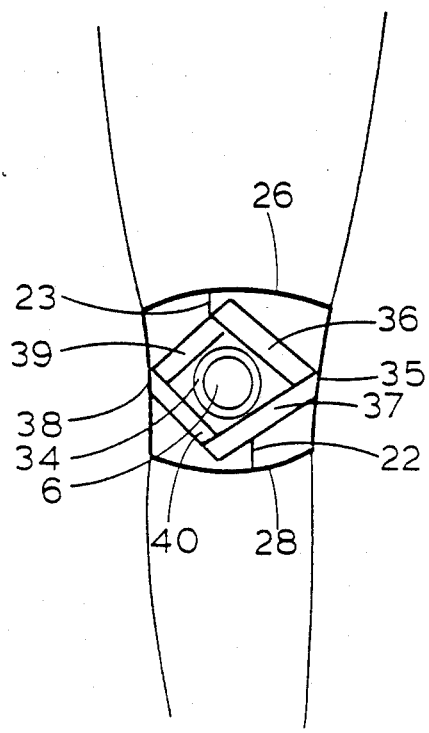
Figure 8:
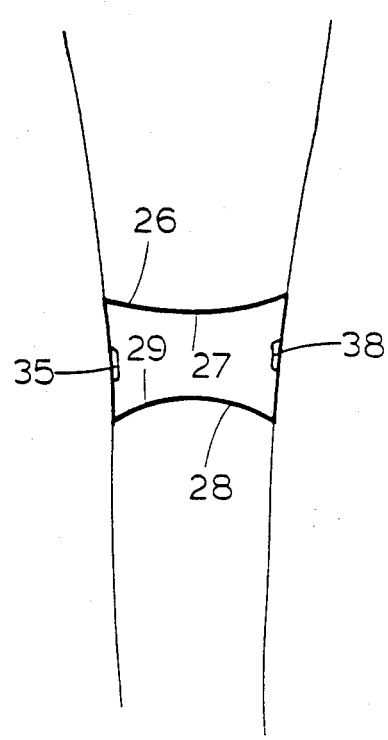

FIG. 1 is a highly diagrammatic view of the positions of muscles (tendons) on the dorsal side of a right knee;

FIG. 2 a highly diagrammatic view of the positions of muscles (tendons) on the ventral side of the knee;

FIG. 3 a top view (outer surface) of a support for a right knee joint according to the invention;

FIG. 4 a bottom view (inner surface) of the support according to FIG. 3;

FIG. 5 a cross section along line V—V in FIG. 4;

FIG. 6 a cross section along line VI—VI in FIG. 4;

FIG. 7 a front view of a right knee with support according to the invention, and FIG. 8 a rear view of the right knee of FIG. 7.

In FIG. 1, respectively FIG. 2, the dorsal, respectively ventral, side of a right knee joint is shown. The reference numbers in these figures are given below with the designated parts stated behind.

1. femur (thigh bone)
2. tibia (shin bone)
3. fibula (calf bone)
4. articular surface of the femur
5. articular surface of the tibia
6. patella (knee cap)
7. m. rectus femoris
8. m. vastus lateralis
9. m. vastus medialis
10. m. sartorius (tailor's muscle)
11. m. gracilis
12. m. semitendinosus (semitendinous muscle)
13. m. semimembranosus (semimembranous muscle)
14. caput longum of the m. biceps femoris
15. caput breve of the m. biceps femoris
16. caput mediale of the m. gastrocnemius
17. caput laterale of the m. gastrocnemius
18. m. plantaris
19. m. popliteus
20. ligamentum collaterale tibiale.

Muscles 7 up to and including 19 all of them extend from their origin to beyond articular surfaces 4 and 5 between femur 1 and tibia 2. If the tonuses of these muscles, which are situated round the knee joint, are increased more or less simultanously, articular surface 4 and 5 are pulled together. The means by which this more or less simultaneous increase of the tonuses can be effected is, for a right knee joint, the support represented in FIGS. 3 up to and including 6. It consists of a subtantially trapezium-shaped wrapper 21 made from a textile material that can be stretched into two directions. The slant sides 22 and 23 are provided with semielliptic recesses 24 and 25. The long or proximal side 26 of the support has a concave, inward bent shape 27. The short or distal side 28 of the support has a concave, inward bent shape 29. When wrapper 21 is formed into a sleeve round the knee, sides 22 and 23 overlap. The fasteners used between slant sides 22 and 23 consist of Velcro (hook and pile) tape, where, as known, a surface with hooks adheres to a surface with loops. Hereinafter the surface with hooks will be referred to as 'hook tape' and the surface with loops as 'pile tape'. For the fastening of the slant sides 22 and 23 pile tape has been applied in parts 30 and 31 on the outer surface of the support (FIG. 3) and hook tape has been applied in parts 32 and 33 of the inner surface of the support (FIG. 4). So the local overlap between pile tape 30 and hook tape 32 is in a direction opposite to that of pile tape 31 and hook tape 33. See also FIG. 7. In the formation of wrapper 21 round the knee by means of the hook-and-pile-tape fasteners described recesses 24 and 25 form an opening 34 to leave knee cap 6 free. See FIG. 7. Wrapper 21 is provided with a medial pair of bandages fastened medially in part 35 and consisting of a proximal bandage 36 and a distal bandage 37 and with a lateral pair of bandages fastened laterally in part 38 and consisting of a proximal bandage 39 and a distal bandage 40. The bandages are provided with fasteners by which they can be fastened to the sleeve formed from the wrapper in positions distal or proximal in respect of opening 34. Here again, these fasteners consist of hook and pile tapes. Bandage 39 is provided, on the side facing the wrapper, with hook tape 41 and on the side away from the wrapper with pile tape 42. Bandage 40 is provided, on the side facing the wrapper, with hook tape 43. Bandage 40 is provided, on the side facing the wrapper, with hook tape 44. Bandage 37 is provided, on the side away from the wrapper, with pile tape 45 and on the side facing the wrapper with hook tape 46. The outer surface of the wrapper is provided with pile tape 47 and pile tape 48. The application and fastening of the support, as well as the pulling and fastening of the bandages, proceed as follows. Hook tape 32 of the wrapper on pile tape 30 of the wrapper, hook tape 33 of the wrapper on pile tape 31 of the wrapper. Hook tape 41 of bandage 39 on pile tape 47 of the wrapper, hook tape 44 of bandage 36 on pile tape 42 of bandage 39, hook tape 46 of bandage 37 on pile tap 48 of the wrapper and hook tape 43 of bandage 40 on pile tape 45 of bandage 37. The continuous application of alternate medial and lateral pulling forces during the fastening of the wrapper and of the bandages contributes to the correct application of the support. This is of particular importance for the position of the parts of the inner surface having an increased coefficient of friction in respect of the skin. The parts of the surface having an increased coefficient of friction in respect of the skin have been drawn in FIG. 4. Along the proximal side 26 are the chamois leather surface parts 49, 50 and 51. On the distal side 28 are chamois leather surface parts 52, 53 and 54. Round the semielliptic openings 24 and 25, except for those parts where hook tapes 33 and 32 have been applied, the chamois leather surface parts 55 and 56 have been provided in such a manner that after the formation into a sleeve the part round the opening formed (see FIG. 7) has a surface of chamois leather. Between the proximal side 26 and distal side 28 are strips 57 and 58. These strips 57 and 58 also constitute parts having a chamois leather surface. In the embodiment drawn they partly coincide with the chamois leather surface parts 55 and 56 round the semielliptic recesses 24 and 25. Round the semi-eliptic recesses 24 and 25 pad-like elevations 59 and 60 have been applied, which are shown in cross section in FIG. 6. In the embodiment of the drawing the chamois leather surface parts 55 and 56 coincide with the pad-like elevations 59 and 60. A central strip 61 extending between the proximal side 26 and the distal side 28 of the support, the circumference of which strip is shown in FIG. 4 by abcd, is in the form of a pad. FIGS. 5 and 6 show that the central strip 61 has the form of a flat pad. FIGS. 5 and 6 show that the pad-like elevations 60 and 59, as well as the pad-like central strip 61, are obtained by applying a resilient filler 62. The dimensions of the central strip in transversal direction are such as to allow the surface of the skin on the dorsal side of the knee area under which muscles, 12, 13 and 14 of FIG. 1 are situated to be covered.

FIG. 7 is a drawing of the front view of a right knee with a support applied. FIG. 8 shows the rear view. With the surface parts that have an increased coefficient of friction, the inner surface of the support covers the surfaces of the skin in the area of the knee joint with, underneath, the muscles and their tendons as drawn in FIGS. 1 and 2. As the support can be applied round the area of the knee joint in a tight fit with the back capable of being pulled well into the hollow of the knee by pulling the bandages, the tendons of the muscles acting on the knee joint are under pressure. With every movement of the lower leg in respect of the leg above the knee, the tendons will be under pressure and be massaged. The curved shapes 27 and 29 of respectively the proximal 26 and the distal 28 side of the support on the dorsal side of the knee (see FIG. 8), causing a local narrowing of the support, to a substantial degree help to apply pressure to the tendons on the dorsal side of the knee joint. The pulling of the bandages enhances the circumferential pressure on the knee cap causing the latter to be raised from its articular surfaces with the femur.

I claim:

1. A support for a knee joint comprising:
a sleeve member made substantially from elastic material and adapted to extend, after its application, between a proximal and a distal line in respect to the knee joint, said support defining an opening for the kneecap; and
a plurality of frictional portions defined on the inner surface of the support, said frictional portions having a greater coefficient of friction in respect of the skin than the coefficient of friction of the other portions of the inner surface of the interior of said sleeve member, said frictional portions being disposed on the portions of the inner surface of the support which are adapted to be disposed in contact, after the application of the support, with portions of the skin surface in the areas around the joint beneath which muscles and tendons are disposed, which muscles and tendons extend from the leg below and the leg above the knee beyond the articular surfaces of the knee between the femur and the tibia, which muscles and tendons can be innervated propioceptively so as to press together skeletal parts situated on either side of the knee joint when the knee is moved and said frictional portions inhibit the movement of skin in contact therewith.

2. A support according to claim 1, said frictional portions consist of chomois leather.

3. A support according to claim 1, wherein at least one of said frictional portions is discontinuous.

4. A support according to claim 1, wherein said frictional portions portions are disposed along the proximal side and the distal side of the support coinciding with the proximal and distal limits of the support, around the opening for the knee cap and on strips extending between the proximal and distal sides of the support and situated medially and laterally in respect of the opening and adjacent the opening.

5. A support suited as support for a knee joint according to claim 4, which support comprises a substantially trapezium-shaped wrapper the slant sides of which are provided with semi-elliptic recesses, which wrapper, using fasteners along the slant sides, can be shaped to form a sleeve with an opening to leave the knee cap free, wherein the proximal side of the support, the long side of the trapezium side of the support, has a concave, inward bent shape at least in its central parts and in that the support is provided with a medial pair of bandages fastened medially near the opening and consisting of a proximal and a distal bandage and with a lateral pair of bandages fastened laterally near the opening and consisting of a proximal and a distal bandage, the proximal and distal bandages having fasteners by which they can be fastened in respectively proximal and distal positions in respect of the opening.

6. A support according to claim 5, wherein pad-like elevations have been applied on the inner surface of the support round the semi-elliptic recesses.

7. A support according to claim 4, wherein on the dorsal side of the support a central strip of the support extending between the proximal and distal sides is in the shape of a pad.

8. A support according to claim 6, wherein the place where the pad-like elevations have been applied round the semielliptic recesses coincides with the place where, round the opening, a part of the surface has an increased coefficient of friction.

9. A support according to claim 11, further comprising bandage means fastened to said sleeve member so as to provide at least one of greater pressure on and more support to the knee joint to which the sleeve member is mounted.

* * * * *

UNITED STATES PATENT AND TRADEMARK OFFICE
CERTIFICATE OF CORRECTION

PATENT NO. : 4,724,831
DATED : February 16, 1988
INVENTOR(S) : Jozef H.G. HUNTJENS It is certified that error appears in the above-identified patent and that said Letters Patent is hereby corrected as shown below:

In Column 3, line 23, "a.3" (first occurrence) should be --a.2.--.

In Column 4, line 1, "folow" should be --follow--.

In Column 8, line 5, "chomois" should be --chamois--.

Signed and Sealed this

Eleventh Day of October, 1988

Attest:

DONALD J. QUIGG

Attesting Officer

Commissioner of Patents and Trademarks